(12) United States Patent
Shaw et al.

(10) Patent No.: US 7,291,743 B2
(45) Date of Patent: Nov. 6, 2007

(54) ISOXAZOLE DERIVATIVES AND METHODS OF TREATING NITRIC OXIDE MEDIATED DISEASES

(75) Inventors: Jiajiu Shaw, Ann Arbor, MI (US); An-Rong Lee, Taipei (TW); Wen-Hsin Huang, Taipei (TW)

(73) Assignee: Geneblue Corporation, Los Angeles, CA (US)

( * ) Notice: Subject to any disclaimer, the term of this patent is extended or adjusted under 35 U.S.C. 154(b) by 37 days.

(21) Appl. No.: 11/093,182

(22) Filed: Mar. 29, 2005

(65) Prior Publication Data

US 2006/0223873 A1    Oct. 5, 2006

(51) Int. Cl.
*C07D 413/10* (2006.01)
*C07D 413/12* (2006.01)
*C07D 261/08* (2006.01)

(52) U.S. Cl. ..................................... 548/248
(58) Field of Classification Search .................. 548/248
See application file for complete search history.

(56) References Cited

U.S. PATENT DOCUMENTS 5,059,614 A    10/1991   Lepage et al.
6,727,272 B1    4/2004   Lee et al.

FOREIGN PATENT DOCUMENTS

WO    WO-2004/006834 A2 *    1/2004

OTHER PUBLICATIONS

CA Registry No. 717866-68-7, entry date into the Registry file on STN is Jul. 28, 2004.*
CA Registry No. 717858-34-9, entry date into the Registry file on STN is Jul. 28, 2004.*
CA Registry No. 688051-07-2, entry date into the Registry file on STN is Jun. 1, 2004.*
Svab et al., CA 100:82623, 1984.*
Svab et al., Cesko-Slovenska Farmacie, (1983), 32(9-10), pp. 316-322.*
Miljkovic, Dj. et al., "Leflunomide Inhibits Activation of Inducible Nitric Oxide Synthase in Rat Astrocytes," *Brain Research*, 2001, 889, 331-338.

* cited by examiner

*Primary Examiner*—Laura L. Stockton
(74) *Attorney, Agent, or Firm*—Butzel Long

(57) ABSTRACT

A series of isoxazole derivatives and methods of suppressing, inhibiting, or preventing disorders mediated by nitric oxide (NO) and/or proinflammatory cytokines, such as TNF-α (tumor necrosis factor alpha), IL-1 (interlukin-1), and IL-6, are described.

1 Claim, No Drawings

ISOXAZOLE DERIVATIVES AND METHODS OF TREATING NITRIC OXIDE MEDIATED DISEASES

FIELD OF THE INVENTION

This invention relates to a series of new chemical entities (NCEs) and methods of suppressing, inhibiting, or preventing disorders mediated by nitric oxide (NO) and/or proinflammatory cytokines, such as TNF-α (tumor necrosis factor alpha), IL-1 (interlukin-1), and IL-6. Examples of these disorders include but are not limited to rheumatoid arthritis, osteoarthritis, lupus, ischemia/reperfusion, Alzheimer's, stroke, and multiple sclerosis.

BACKGROUND

Historically, the role of NO in human health was thought to be primarily as an irritant in air pollution. This view changed dramatically in 1987 with the discovery of the production of NO in the body and the identification of the molecule's key role in biological signaling. Since 1987, thousands of scientific papers on NO have been published, which attests to the intensity of research interest devoted to this molecule. In recognition of the medical significance of the molecule, the 1998 Nobel Prize in Physiology was awarded to the scientists who discovered the role of NO as a biological messenger.

NO is a molecular messenger synthesized by nitric oxide synthase (NOS) from L-arginine and oxygen. NO is involved in a number of physiological and pathological processes in mammalians. Three structurally distinct isoforms of NOS have been identified: neuro (nNOS), endothelial (eNOS), and inducible (iNOS).

NO is a small gaseous molecule with chemical properties that make it uniquely suitable as both an intra- and intercellular messenger. Because it possesses an unpaired election, NO reacts with other molecules with unpaired electrons, especially superoxide, which can combine with NO to form peroxynitrite, a highly reactive and toxic radical. As a neutral gaseous molecule, NO can diffuse over several cell lengths from its source to exert control over certain enzymes and regulate key cellular functions. The combined properties of its ability to regulate enzymes across long distances as well as its high reactivity with other molecules give NO its unique dual role as both a powerful signaling molecule and a lethal effector molecule.

Because of these powerful functions, the production of NO is tightly regulated and there is ample literature to show that too little or too much NO production contributes to numerous human diseases and disorders.

NO is a potent pleiotropic mediator of physiological processes such as smooth muscle relaxation, neuronal signaling, inhibition of platelet aggregation and regulation of cell mediated toxicity. It is a diffusible free radical which plays many roles as an effector molecule in diverse biological systems including neuronal messenger, vasodilation and antimicrobial and antitumor activities. NO appears to have both neurotoxic and neuroprotective effects and may have a role in the pathogenesis of stroke and other neurodegenerative diseases, in demyelinating conditions (e.g., multiple sclerosis), in ischemia and traumatic injuries associated with infiltrating macrophages, and in the production of proinflamatory cytokines. A number of pro-inflammatory cytokines and endotoxin (bacterial lipopolysaccharide, LPS) also induce the expression of inducible nitric oxide synthase (iNOS) in a number of cells, including macrophages, vascular smooth muscle cells, epithelial cells, fibroblasts, glial cells, cardiac myocytes as well as vascular and non-vascular smooth muscle cells.

Although NO mediates a number of physiological functions, overproduction of NO has been reported in a number of clinical disorders. Therefore, maintaining suitable levels of NO is very important. For example, decreased NO generation in the penis results in impotence. On the other hand, many other diseases and conditions such as intradialytic hypotension, hemorrhagic shock, tissue rejection, rheumatoid arthritis, and diabetes are associated with the overproduction of NO.

There is now substantial evidence that excess NO production is involved in a number of conditions, including conditions that involve systemic hypotension such as septic and toxic shock and therapy with certain cytokines. Circulatory shock of various etiologies is associated with profound changes in the body's NO homeostasis. In animal models of endotoxic shock, endotoxin produces an acute release of NO from the constitutive isoform of nitric oxide synthase in the early phase, which is followed by induction of iNOS. NO derived from macrophages, microglia and astrocytes has been implicated in the damage of myelin producing oligodendrocytes in demyelinating disorders like multiple sclerosis and neuronal death during neuronal degenerating conditions including brain trauma.

Cytokines associated with extracellular signaling are involved in the normal process of host defense against infections and injury, in mechanisms of autoimmunity, and in the pathogenesis of chronic inflammatory diseases. It is known that NO mediates deleterious effects of the cytokines. For example, NO as a result of stimuli by cytokines (e.g., TNF-α, IL-1, and/or IL-6) is implicated in autoimmune diseases such as multiple sclerosis, rheumatoid arthritis, osteoarthritis, inflammatory bowel disease, systemic lupus erythematosus, and diabetes. The NO produced by iNOS is associated with bactericidal properties of macrophages. Recently, an increasing number of cells (including muscle cells, macrophages, keratinocytes, hepatocytes and brain cells) have been shown to induce iNOS in response to a series of proinflammnatory cytokines including IL-1, TNF-α, interferon-γ (IFN-γ) and bacterial lipopolysaccharides (LPS).

There are several drugs being used to treat diseases associated with the overproduction of NO and/or cytokines. The present invention relates to the significant improvement on a marketed drug, leflunomide (marketed as Arava® by Aventis Pharmaceuticals).

Leflunomide has been approved for treating rheumatoid arthritis (RA) by the Food and Drug Administration (FDA) since 1998. Recently, it was approved for an additional indication, improvement in physical function. Currently, leflunomide is being developed for multiple sclerosis.

Highly reactive NO, generated by astrocytes and infiltrating macrophages, is implicated in inflammatory destruction of brain tissue, including that occurring in multiple sclerosis. Leflunomide was shown to inhibit activation of iNOS in rat astrocytes. (Miljkovic D. et al., "Leflunomide inhibits activation of inducible nitric oxide synthase in rat astrocytes". Brain Res. Jan. 19, 2001; 889(1-2): 331-8.)

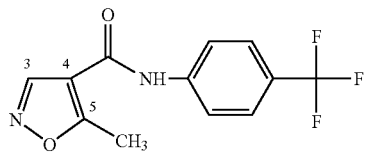

Leflunomide (Arava®)

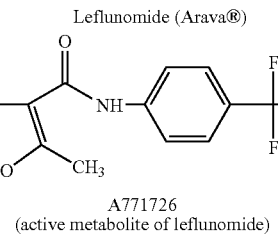

A771726
(active metabolite of leflunomide)

DETAILED DESCRIPTION

The present invention provides a number of isoxazole derivatives that are distinctively different from leflunomide and all other isoxazole derivatives (see: "Leflunomide analogs for treating rheumatoid arthritis," An-Rong Lee et al., U.S. Pat. No. 6,727,272, Apr. 27, 2004; "Novel isoxazole and isoxazoleline compounds with anticonvulsant activity process for their preparation and therapeutic composition containing them," Francis Lepage et al., U.S. Pat. No. 5,059,614, Oct. 22, 1991).

The present invention provides a series of isoxazole derivatives based on the innovative modifications on leflunomide. As shown in Example 5, study results indicate that these isoxazole derivatives are surprisingly effective in lowering NO in vitro as compared to leflunomide and its metabolite, A771726.

The present invention provides a compound of formula (I) or a physiological tolerable salt of the compound of formula (I) shown below:

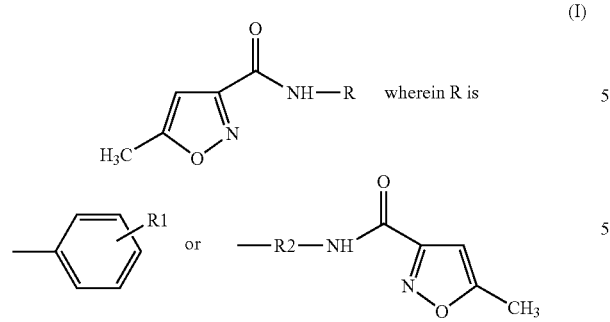

wherein R1 is ortho-OH, meta-OH, para-OH, ortho-OCH$_3$, meta-OCH$_3$, para-OCH$_3$, ortho-O—CO—CH$_3$, meta-O—CO—CH$_3$, para-O—CO—CH$_3$, ortho-NO$_2$, meta-NO$_2$, para-NO$_2$, ortho-NH$_2$, meta-NH$_2$, para-NH$_2$, ortho-NH-COCH$_3$, meta-NHCOCH$_3$, para-NHCOCH$_3$, or one of the following:

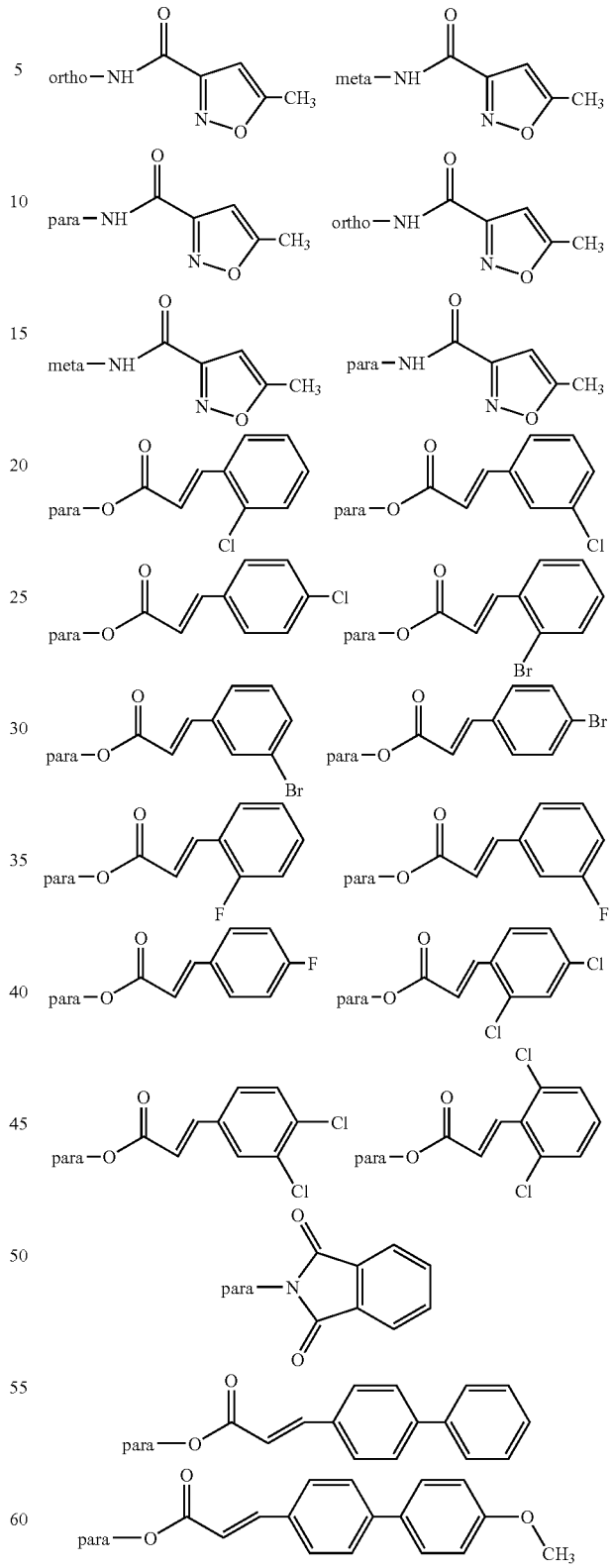

and wherein R2 is lower alkyl or substituted lower alkyl. As used herein, the phrase "lower alkyl" means a linear, branched, or cyclic hydrocarbon group about 1 to 6 carbons, preferably from 3 to 6 carbons. The phrase "substituted lower alky" means lower alkyl with one or more —OH, —COOH, —NH$_2$, —NO$_2$, or —CO— groups.

The present invention discloses a pharmaceutical composition comprising the compound of formula (I) or a physiological tolerable salt of the compound of formula (I). The pharmaceutical composition comprises an effective amount of at least one compound of formula (I) or a physiologically tolerable salt of the compound of formula (I) and pharmaceutically suitable excipients, additives, and/or other active compounds and auxiliaries.

The present invention provides methods of treating a nitric oxide or cytokine mediated disease, comprising administering a biologically effective amount of at least one compound of formula (I) or a physiologically tolerable salt of the compound of formula (I). The compound or salt may be formulated with pharmaceutically acceptable excipients, additives, and/or other active compounds and auxiliaries. The cytokine is selected from the group consisting of TNF-α (tumor necrosis factor-α), IL-1β (interleukin-1β), IL-6, IL-2, IL-8, IFN-γ (interferon-γ), and combinations thereof. The disease comprises Rheumatoid arthritis, osteoarthritis, inflammatory bowel disease, systemic lupus erythematosus, psoriasis, septic shock, diabetes, chronic obstructive pulmonary disease (COPD), asthma, allergy, migraine, ischemia, atherosclerosis, Alzheimer's disease, Parkinson's disease, multiple sclerosis, ankylosing spondylitis, and combinations thereof.

Representative examples of the compound of formula (I) are shown below:

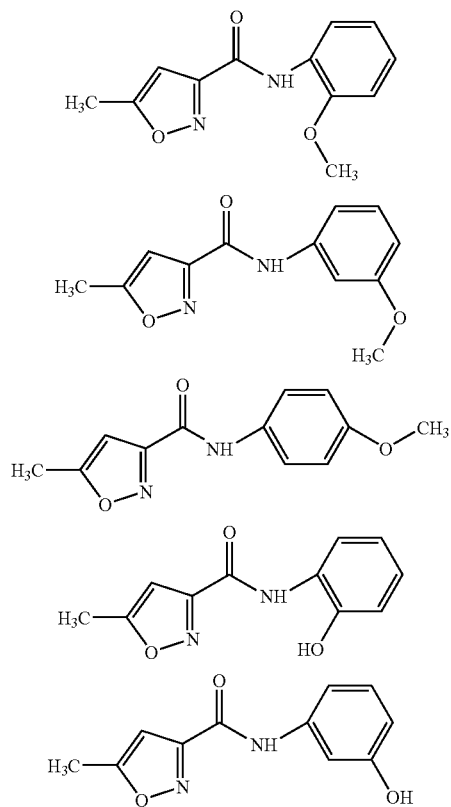

-continued

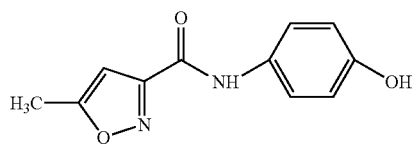
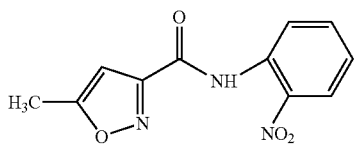
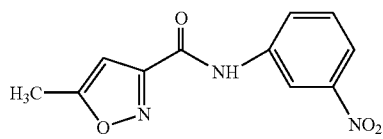
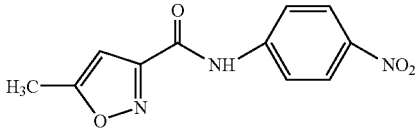
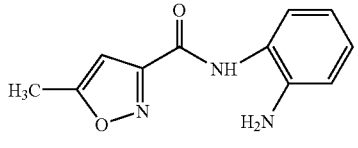
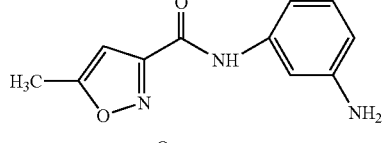
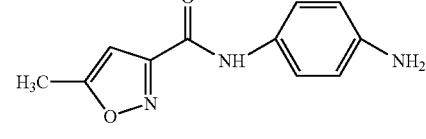
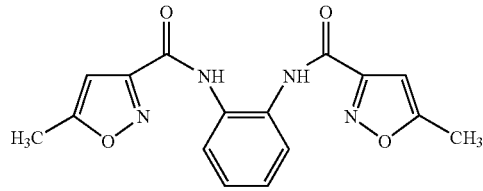
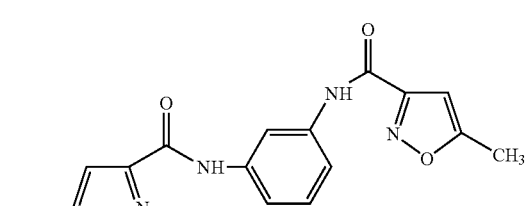
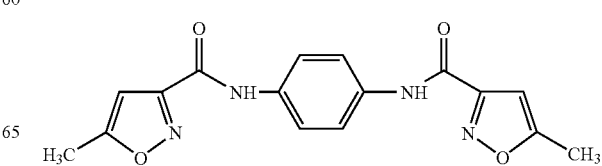

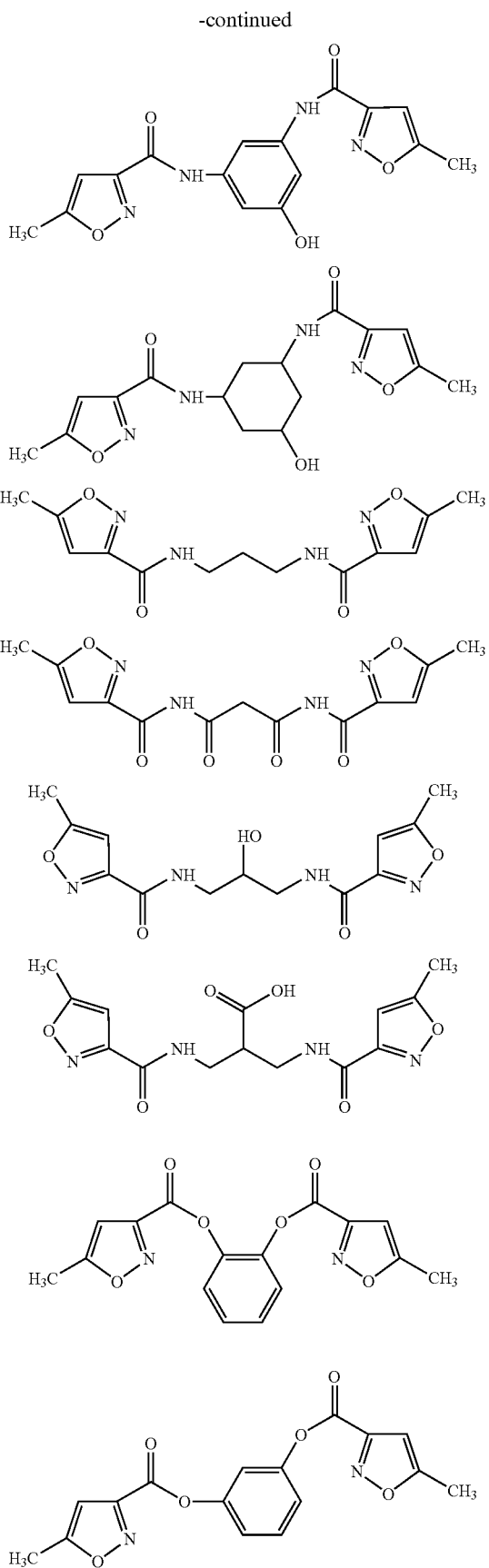

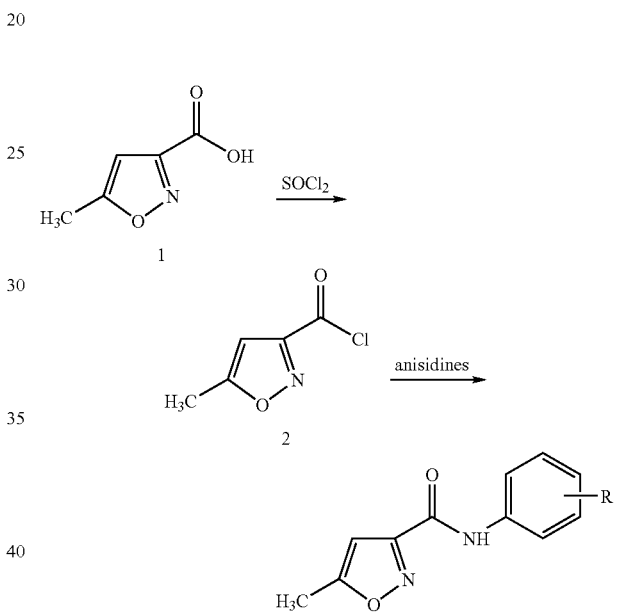

The following representative procedures and Examples, including specific examples of the synthesis and modulation of NO, are provided solely by way of illustration, and are not intended to limit the scope of the appended claims or their equivalents.

EXAMPLE 1

Synthesis of Compound 3a, 3b, or 3c

Compound 1 (5-methylisoxazole-3-carboxylic acid) (1.27 g, 10 mmole) was refluxed in 10 mL of toluene with thionyl chloride (10 mL) for 3 hr. The excess thionyl chloride was removed in vacuo to make compound 2. Anisidines (1.23 g, 10 mmole) and triethylamine (TEA)(1.39 mL, 10 mmole) were added to compound 2 in 10 mL of dichloromethane. The mixture was stirred at room temp for 10 min and the solvent was removed in vacuo. After acidification with diluted HCl, the mixture was poured into water and then extracted with ethyl acetate a couple times. The combined organic layers were dried by Molecular Sieve and concentrated. Recrystallization in ethanol afforded compound 3a-c.

| Compound | R | Yield (%) | Color | m.p. (° C.) | CHN based on $C_{12}H_{12}N_2O_3$ (%) |
|---|---|---|---|---|---|
| 3a | 2-OCH$_3$ | 92 | white | 78-80 | Theory: C 62.06, H 5.21, N 12.06 Found: C 61.82, H 5.71, N 11.37 |

| Compound | R | Yield (%) | Color | m.p. (° C.) | CHN based on $C_{12}H_{12}N_2O_3$ (%) |
|---|---|---|---|---|---|
| 3b | 3-OCH$_3$ | 89 | white | 96-98 | Theory: C 60.55, H 4.62, N 12.84 Found: C 61.61, H 5.72, N 11.12 |
| 3c | 4-OCH$_3$ | 93 | white | 124-126 | Theory: C 60.55, H 4.62, N 12.84 Found: C 62.12, H 5.23, N 12.33 |

EXAMPLE 2

Synthesis of Compound 4a, 4b, or 4c

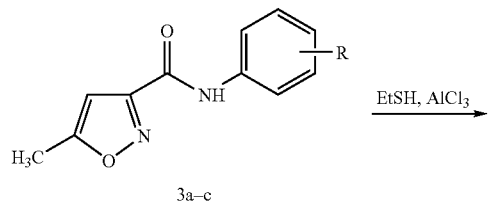

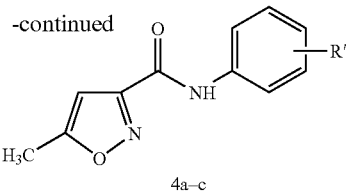

Compound 3a-c (1.16 g, 5 mmole) in 30 mL of dichloromethane was added ethanethiol (EtSH) (1.55 g, 25 mmole) and AlCl$_3$ (4.99 g, 37.5 mmole). The mixture was stirred at room temp for 20 mm and poured into ice-water to precipitate the product. After filtration, the product was washed with ice-water until free from acid. Recrystallization in dichloromethane afforded compound 4a-c.

| Compound | R | Yield (%) | Color | m.p. (° C.) | CHN based on $C_{11}H_{10}N_2O_3$ (%) |
|---|---|---|---|---|---|
| 4a | 2-OH | 77 | white | 158-160 | Theory: C 60.55, H 4.62, N 12.84 Found: C 59.72, H 5.19, N 12.04 |
| 4b | 3-OH | 80 | white | 140-142 | Theory: C 60.55, H 4.62, N 12.84 Found: C 59.46, H 5.03, N 11.49 |
| 4c | 4-OH | 82 | white | 158-160 | Theory: C 60.55, H 4.62, N 12.84 Found: C 61.58, H 4.22, N 12.85 |

EXAMPLE 3

Synthesis of Compound 14a, 14b, or 14c

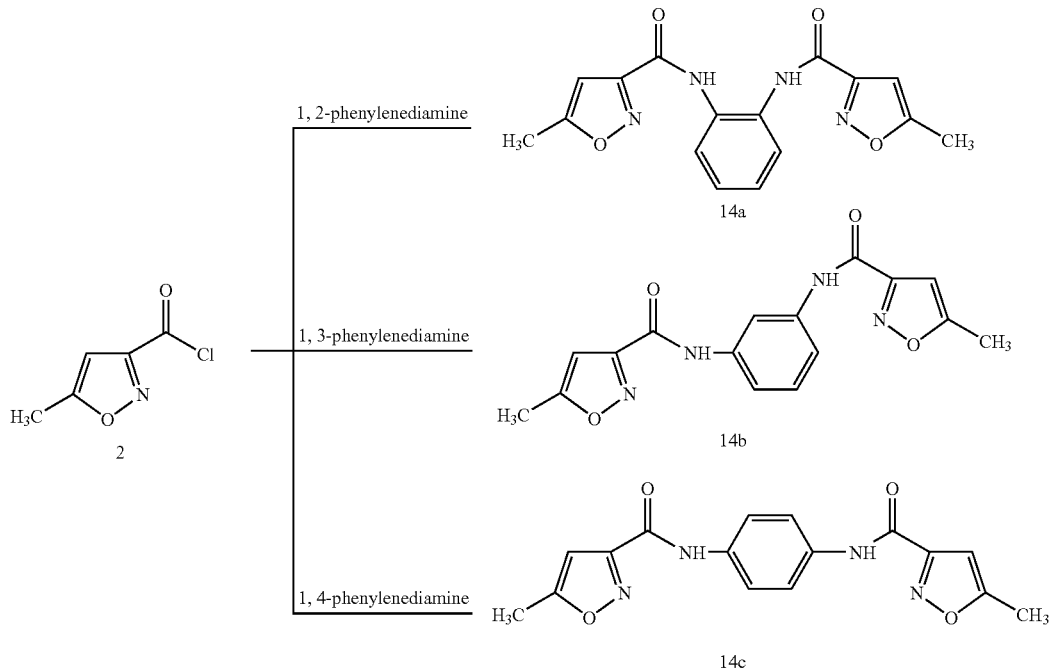

5-methylisoxazole-3-carboxylic acid (1.27 g, 10 mmole) was refluxed with thionyl chloride (10 mL) in 10 mL toluene for 3 hr. The excess thionyl chloride was removed in vacuo to provide compound 2 (as shown in example 1). Phenyl-ethylenediamine (1.1 g, 10 mmole) and TEA (1.39 mL, 10 mmole) were added to compound 2 in dichloromethane (10 mL). The mixture was stirred at room temp for 30 min and dichloromethane was removed in vacuo. After acidification with dilute HCl, the mixture was poured into water to precipitate the product. Recrystallization in ethanol afforded pure compound 14a-c.

| Compound | Yield (%) | Color | m.p. (° C.) | CHN based on $C_{16}H_{14}N_4O_4$ (%) |
|---|---|---|---|---|
| 14a | 83 | white | 190-192 | Theory: C 58.89, H 4.32, N 17.17 Found: C 58.10, H 4.05, N 17.32 |
| 14b | 72 | Gray | 192-194 | Theory: C 58.89, H 4.32, N 17.17 Found: C 58.78, H 4.16, N 16.88 |
| 14c | 74 | white | 178-180 | Theory: C 58.89, H 4.32, N 17.17 Found: C 58.85, H 3.95, N 16.97 |

EXAMPLE 4

Synthesis of Compound 15 a, 15b, or 15c

| Compound | Yield (%) | Color | m.p. (° C.) | CHN based on $C_{16}H_{12}N_2O_6$ (%) |
|---|---|---|---|---|
| 15a | 72 | white | 88-90 | Theory: C 58.54, H 3.28, N 8.53 Found: C 58.56, H 2.94, N 8.47 |
| 15b | 81 | white | 136-138 | Theory: C 58.54, H 3.28, N 8.53 Found: C 58.59, H 3.16, N 8.52 |
| 15c | 70 | white | 148-150 | Theory: C 58.54, H 3.28, N 8.53 Found: C 58.61, H 2.68, N 8.53 |

EXAMPLE 5

Inhibition of Nitric Oxide Production in vitro
Procedure

1. Prepare the cell culture medium DMEM (Dulbecco's modified eagle medium) with 10% fetal calf serum and 10% penicillin-streptomycin. Grow RAW264.7 cells (murine macrophage) in the medium in an incubator at 37° C. under 5% $CO_2$ and saturated water vapor.
2. Dissolve each test compound in DMSO to make a stock solution. Prepare the test solutions by making suitable dilutions of each stock solution with DMEM.
3. Add the LPS solution (final concentration=1 μg/mL) and the test solution (final concentration ranging from

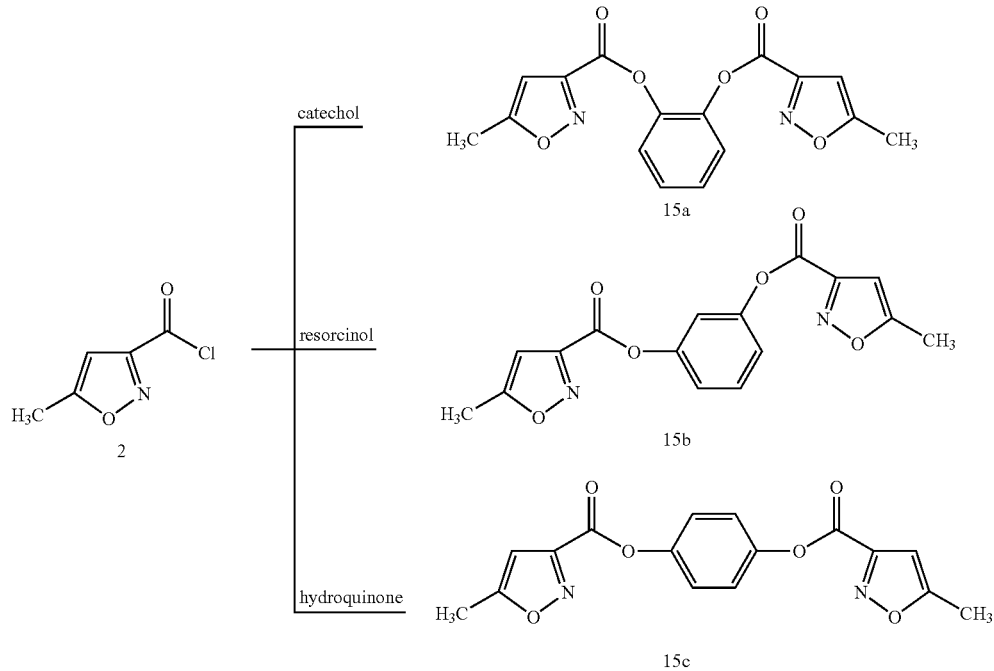

5-methylisoxazole-3-carboxylic acid (1.27 g, 10 mmole) was refluxed with thionyl chloride (10 mL) in 10 mL toluene for 3 hr. The excess thionyl chloride was removed in vacuo to provide compound 2 (as shown in example 1). Phenyldiol (1.1 g, 10 mmole) and TEA (1.39 mL, 10 mmole) were added to compound 2 in dichloromethane (10 mL). The mixture was stirred at room temp for 30 min and 25, 50, 100, and up to 200 μM) to individual cell cultures and place in the incubator for 24 hours.
4. In vitro Nitrite quantification: The production of NO was determined by measuring the accumulated levels of nitrite in culture supernatants with the Griess reagent in LPS-stimulated macrophage cells.
  (a) Withdraw 100 μL of the medium from each cell culture and place in a 96-well plate microplate. Add 100 μL of Griess reagent to the medium at room temperature and cover with aluminum foil for 10 minutes.

(b) Measure the absorption by a Dynatech ELISA reader at 550 nm. NaNO$_2$ was used as the standard to calculate the nitrite concentration.

(c) Calculate the % inhibiiton by the following equation:

$$\text{Inhibition \%} = \frac{R_{M+L} - R_{M+L+C}}{R_{M+L} - R_M} \times 100\%$$

Wherein $R_M$ is the reading of medium only, $R_{M+L}$ is the reading of medium with LPS, $R_{M+L+C}$ is the reading of medium with LPS and test compound.

Results:

| Results shown are Mean ± S.E. of 4-6 observations ($*P < 0.05, **P < 0.001$). | |
| --- | --- |
| Compound | IC$_{50}$ (μM) |
| leflunomide | 298.0 ± 10.1* |
| A771726 | 175.3 ± 4.7* |
| 3a | 99.3 ± 0.9* |
| 3b | 110.8 ± 1.8* |
| 3c | >500 |
| 4a | 1.4 ± 0.1* |
| 4b | 7.7 ± 0.2* |
| 4c | 6.3 ± 0.1* |
| 14a | 7.2 ± 0.8* |
| 14b | 19.4 ± 0.3* |
| 14c | 0.6 ± 0.01* |
| 15a | 4.5 ± 0.4* |
| 15b | 26.8 ± 0.3* |
| 15c | 7.6 ± 0.4* |

The results showed that the compounds embodying features of the present invention are associated with much lower IC$_{50}$ values in vitro as compared to UTL-5b, leflunomide and leflunomide's metabolite, A771726, indicating that these improved isoxazole derivatives are more effective in lowering LPS-induced production of NO

SUMMARY, RAMIFICATION, AND SCOPE

In conclusion, the present invention provides syntheses of a series of novel derivatives of isoxazole, which have not been disclosed by other parties.

In addition, the present invention provides methods of treating disorders mediated by the overproduction of NO or mediated by the overexpression of cytokines. Because the biology of NO in many other diseases is yet to be explored, there is the potential for the compounds embodying features of the present invention to address yet additional diseases.

Although the description above contains many specificities, these should not be construed as limiting the scope of the invention but as merely providing the illustrations of some of the presently preferred embodiments of this invention. Thus the scope of this invention should be determined by the appended claims and their legal equivalents, rather than by the examples given.

The invention claimed is:

1. A compound of formula (I):

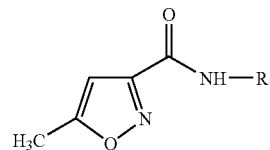

or a physiological tolerable salt thereof;
wherein R is

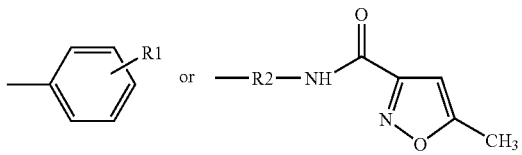

wherein R1 is selected from the group consisting of

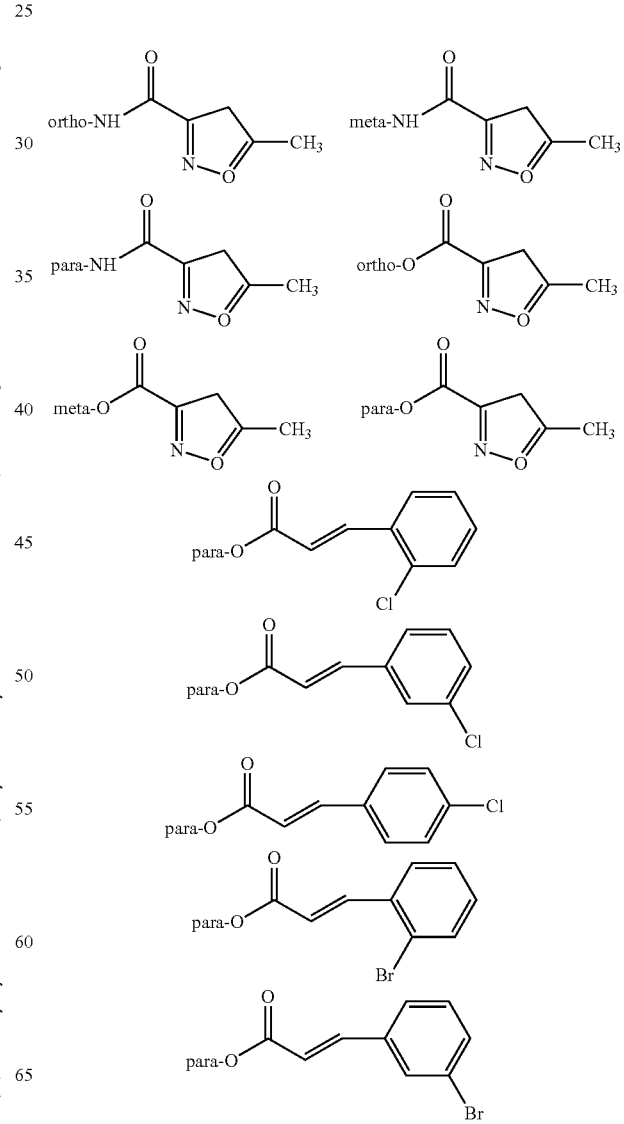

-continued
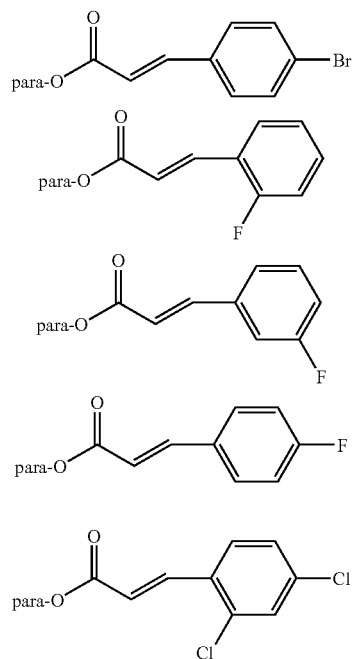
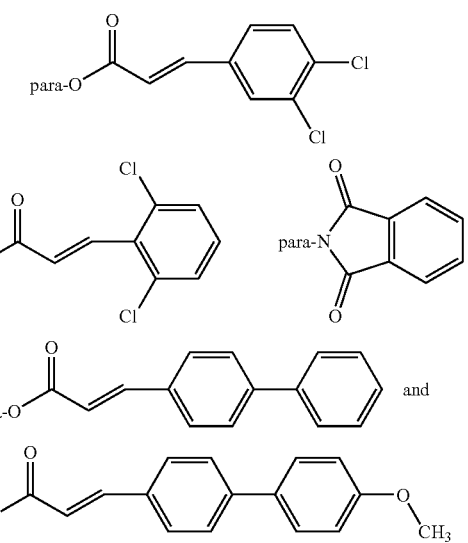
wherein R2 is lower alkyl or substituted lower alkyl.
* * * * *

UNITED STATES PATENT AND TRADEMARK OFFICE
CERTIFICATE OF CORRECTION

| | | |
|---|---|---|
| PATENT NO. | : 7,291,743 B2 | Page 1 of 1 |
| APPLICATION NO. | : 11/093182 | |
| DATED | : November 6, 2007 | |
| INVENTOR(S) | : Jiajiu Shaw, An-Rong Lee and Wen-Hsin Huang | |

It is certified that error appears in the above-identified patent and that said Letters Patent is hereby corrected as shown below:

Line 67, column 11 omits text from the original specification and should be changed to read as follows:

--mixture was stirred at room temp for 30 min and "dichloromethane was removed in vacuo. After acidification with dilute HCl, the mixture was poured into water to precipitate the product. Recrystallization in ethanol afforded pure compound 15a-c.--

Signed and Sealed this

Thirteenth Day of May, 2008

JON W. DUDAS
*Director of the United States Patent and Trademark Office*